(12) United States Patent
Kalum

(10) Patent No.: US 9,169,474 B2
(45) Date of Patent: Oct. 27, 2015

(54) METHOD FOR PRODUCING A YEAST EXTRACT

(75) Inventor: Lisbeth Kalum, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 1056 days.

(21) Appl. No.: 12/517,417

(22) PCT Filed: Dec. 20, 2007

(86) PCT No.: PCT/EP2007/064353
§ 371 (c)(1),
(2), (4) Date: Jun. 3, 2009

(87) PCT Pub. No.: WO2008/077890
PCT Pub. Date: Jul. 3, 2008

(65) Prior Publication Data
US 2010/0093025 A1    Apr. 15, 2010

Related U.S. Application Data

(60) Provisional application No. 60/871,505, filed on Dec. 22, 2006.

(30) Foreign Application Priority Data

Dec. 22, 2006 (DK) .............................. PA200601699

(51) Int. Cl.
*C12N 1/06* (2006.01)
*C12N 9/52* (2006.01)

(52) U.S. Cl.
CPC . *C12N 9/52* (2013.01); *C12N 1/063* (2013.01)

(58) Field of Classification Search
None
See application file for complete search history.

(56) References Cited

U.S. PATENT DOCUMENTS

| | | | |
|---|---|---|---|
| 6,855,548 B2 * | 2/2005 | Sjoeholm et al. ............. | 435/422 |
| 7,179,630 B2 * | 2/2007 | Lassen et al. ................. | 435/212 |
| 7,485,447 B2 * | 2/2009 | Lassen .......................... | 435/220 |
| 7,588,926 B2 * | 9/2009 | Oestergaard et al. ......... | 435/223 |
| 7,658,965 B2 * | 2/2010 | Sjoeholm et al. ............. | 426/656 |
| 2007/0292938 A1 | 12/2007 | Kalum et al. | |
| 2009/0047387 A1 * | 2/2009 | De Maria et al. .............. | 426/63 |
| 2010/0093025 A1 * | 4/2010 | Kalum .......................... | 435/68.1 |
| 2010/0322915 A1 * | 12/2010 | Svendsen et al. .......... | 424/94.61 |
| 2011/0097445 A1 * | 4/2011 | De Maria et al. ............... | 426/63 |
| 2011/0097448 A1 * | 4/2011 | Wong et al. ..................... | 426/72 |
| 2011/0124084 A1 * | 5/2011 | Oestergaard et al. ......... | 435/212 |
| 2012/0058219 A1 * | 3/2012 | Kreisz et al. .................... | 426/12 |
| 2015/0026843 A1 * | 1/2015 | Hoff et al. ..................... | 800/298 |

FOREIGN PATENT DOCUMENTS

| | | |
|---|---|---|
| EP | 0 354 610 | 2/1990 |
| EP | 1 199 353 | 4/2002 |
| WO | WO 88/03947 | 6/1988 |
| WO | WO 01/58276 | 8/2001 |
| WO | 2004072221 A2 | 8/2004 |
| WO | WO 2004/072221 A2 * | 8/2004 |
| WO | WO 2004/072279 | 8/2004 |
| WO | WO 2004/111220 | 12/2004 |
| WO | WO 2004/111222 | 12/2004 |
| WO | WO 2004/111223 | 12/2004 |
| WO | WO 2005/123911 | 12/2005 |
| WO | WO 2007/042577 A2 * | 4/2007 |
| WO | WO 2007/128766 A2 * | 11/2007 |
| WO | WO 2008/077890 A1 * | 7/2008 |
| WO | WO 2009/147105 A2 * | 12/2009 |
| WO | WO 2010/112546 A2 * | 10/2010 |
| WO | WO 2011/000824 A2 * | 1/2011 |

OTHER PUBLICATIONS

Zeng et al, Shipin Yu Fajiao Gongye, 2004, 30/8:25-39 (abstract only).*
Burgess et al., JCB, 1990, 111:2129-2138.*
Bowie et al. Science, 1990, 247/4948:1306- 1310.*
Lazar et al., Molecular and Cellular Biology, 1988, 8:1247-1252.*
Thomas E. Creighton, In: "Proteins: Structures and Molecular Properties, 1984", pp. 314-315.*
Kumar et al. PNAS 87: 1337-1341 Feb. 1991.*
Thomas E. Creighton, In: Protein Structure: A Practical Approach, 1989; pp. 184-186.*
Nosoh, Y. et al in "Protein Stability and Stabilization through Protein Engineering, 1991" (chapter 7, p. 197).*
Chae et al, Bioresource Technology, vol. 76, No. 3, pp. 253-258 (2001).
Conway et al, Can. J. Microbiol, vol. 47, No. 1, pp. 18-24 (2001).
M. Kelly, Yeast Extract, Chapter 4.24, pp. 457-465 (1982).
Godfrey (ed), 1982, Industrial Enzymology, Stockton Press, London, pp. 457-465.
Mitsuiki et al., Accession No. AA006113, 2014.

* cited by examiner

*Primary Examiner* — Nita M Minnifield
(74) *Attorney, Agent, or Firm* — Kristin J. McNamara

(57) ABSTRACT

The present invention relates to a method for producing a yeast extract using an exogenous protease.

12 Claims, No Drawings

SEQUENCE LISTING

<160> NUMBER OF SEQ ID NOS: 1

<210> SEQ ID NO 1
<211> LENGTH: 188
<212> TYPE: PRT
<213> ORGANISM: Nocardiopsis species

```
<400> SEQUENCE: 1

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25              30

Ala Gly His Cys Gly Arg Val Gly Thr Gln Val Thr Ile Gly Asn Gly
        35              40                  45

Arg Gly Val Phe Glu Gln Ser Val Phe Pro Gly Asn Asp Ala Ala Phe
    50              55                  60

Val Arg Gly Thr Ser Asn Phe Thr Leu Thr Asn Leu Val Ser Arg Tyr
65              70                  75                  80

Asn Thr Gly Gly Tyr Ala Thr Val Ala Gly His Asn Gln Ala Pro Ile
                85              90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
            165                 170                 175

Pro Met Val Asn Ser Trp Gly Val Arg Leu Arg Thr
            180                 185
```

METHOD FOR PRODUCING A YEAST EXTRACT

CROSS-REFERENCE TO RELATED APPLICATIONS

This application is a 35 U.S.C. 371 national application of PCT/EP2007/064353 filed Dec. 20, 2007, which claims priority or the benefit under 35 U.S.C. 119 of Danish application no. PA 2006 01699 filed Dec. 22, 2006 and of U.S. provisional application No. 60/871,505 filed Dec. 22, 2006, the contents of which are fully incorporated herein by reference.

TECHNICAL FIELD

The present invention relates to a method for producing a yeast extract using an exogenous protease.

BACKGROUND OF THE INVENTION

Yeast extracts are widely used, e.g. for flavour in the food industries, in microorganism fermentation media, and as health foods. The production of yeast extract is described in literature, see e.g. Kelly, M. (1982) Yeast Extract (In: Industrial Enzymology, Godfrey, T. ed.) or Chae, H. J. et al. (2001), Bioresource Technology 76, 253-258. It is typically manufactured by breaking down the yeast by acid hydrolysis or mechanical or chemical disruption of the cells followed by autolysis with endogenous enzymes to degrade the macromolecular structures of the yeast, in particular the proteins, into the maximum amount of soluble material. Possibly, exogenous enzymes, including proteases such as papain, are added to augment the effect of the yeast's own enzymes. After the enzymatic hydrolysis, the yeast extract is separated from the cell debris and possibly pasteurized and concentrated. Turbidity is a quality measure of the yeast extract. Low turbidity makes concentration and separation easier. Therefore, there is a desire for methods to produce yeast extracts with low turbidity.

Proteases found to be applicable according to the present invention have been previously described. E.g., the protease derived from *Nocardiopsis* sp. NRRL 18262 is disclosed in WO88/03947 (here the strain is referred to as *Nocardiopsis* sp. strain 10R) and WO01/58276. Other related proteases which are useful according to the invention are disclosed in WO88/03947, WO04/111220, WO04/111222, WO04/111223, WO05/123911, and WO04/072279.

SUMMARY OF THE INVENTION

The present inventor has identified proteases which are found to be applicable in making yeast extracts at high yield with very low turbidity. Such proteases are more efficient than other proteases used in the art when compared to an equal amount of enzyme protein, which results in better product economy for the producers of yeast extracts. In addition, the protein content of the total dry solids is high when the yeast extract is prepared with the proteases of the present invention, which reflects a high purity. Consequently, the present invention relates to a method for producing a yeast extract, comprising: a) adding to yeast comprising protein a protease having at least 50% identity to SEQ ID NO: 1; and b) incubating so as to hydrolyse the protein.

DETAILED DISCLOSURE OF THE INVENTION

Protease

The term protease as used herein is an enzyme that hydrolyses peptide bonds (has protease activity). Proteases are also called, e.g., peptidases, proteinases, peptide hydrolases, or proteolytic enzymes.

The proteases for use according to the invention are of the endo-type that act internally in polypeptide chains (endopeptidases).

There are no limitations on the origin of the protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e.g. by site-directed mutagenesis, by PCR (using a PCR fragment containing the desired mutation as one of the primers in the PCR reactions), or by random mutagenesis. The preparation of consensus proteins is described in e.g. EP 897985. Examples of protease variants, as used in the present context, are proteases in which one or more amino acids have been deleted, inserted or substituted with other amino acids.

Examples of proteases for use according to the invention are
(i) the protease derived from *Nocardiopsis* sp. NRRL 18262, disclosed in WO01/58276, the sequence of which is shown in SEQ ID NO: 1 of the present document;
(ii) proteases having at least 50, 55, 60, 65, 70, 75, 80, 85, 90, or at least 95% amino acid identity to the protease of (i);
(iii) mutants, variants or fragments of the proteases of (i) or (ii) exhibiting protease activity.

For purposes of the present invention, the alignment of two amino acid sequences can be determined by using the Needle program from the EMBOSS package (available at emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between two amino acid sequences is calculated as the number of exact matches in an alignment of the two sequences, divided by the length of the shortest of the two sequences. The result is expressed in percent identity.

An exact match occurs when the two sequences have identical amino acid residues in the same positions of the overlap. The length of a sequence is the number of amino acid residues in the sequence (e.g. the length of SEQ ID NO: 1 is 188).

As examples of bacterial proteases applicable for use according to the invention can be mentioned the protease from *Nocardiopsis alba* (previously *Nocardiopsis dassonvillei*) NRRL 18133 disclosed in WO88/03947, the proteases from *Nocardiopsis dassonvillei* subsp. dassonvillei DSM 43235, *Nocardiopsis alba* DSM 15647, *Nocardiopsis* sp. DSM 16424 and the synthetic Protease 22, all four disclosed in WO04/111220, the protease from *Nocardiopsis prasina* DSM 15648 disclosed in WO04/111222, the protease from *Nocardiopsis prasina* DSM 15649 disclosed in WO04/111223, the proteases from *Nocardiopsis prasina* (previously *Nocardiopsis alba*) DSM 14010, *Nocardiopsis alkaliphila* DSM 44657 and *Nocardiopsis lucentensis* DSM 44048, all three disclosed in WO05/123911, the proteases from *Brachysporiella gayana* CGMCC 0865, *Metarhizium anisopliae*, *Gliocladium* sp. CBS 114001, *Periconia* sp. CBS 114002, *Periconia* sp. CBS 114000 and *Curvularia lunata* CBS 114003, all 6 disclosed in WO04/072279, and mutants, variants or fragments of any of these exhibiting protease activity.

A protease for use according to the invention is a bacterial protease, the term bacterial indicating that the protease is derived from, or originates from, a bacteria, or is an analogue, a fragment, a variant, a mutant, or a synthetic protease derived from a bacteria. It may be produced or expressed in the original wild-type bacterial strain, in another microbial strain, or in a plant; i.e. the term covers the expression of wild-type, naturally occurring proteases, as well as expression in any host of recombinant, genetically engineered or synthetic proteases.

In the process of the invention the protease may be purified. The term "purified" as used herein covers enzyme protein essentially free from components from the organism from which it is derived. The term "purified" also covers enzyme protein free from components from the native organism from which it is obtained, this is also termed "essentially pure" enzyme and may be particularly relevant for enzymes which are naturally occurring and which have not been modified genetically, such as by deletion, substitution or insertion of one or more amino acid residues.

Accordingly, a protease may be purified, viz. only minor amounts of other proteins being present. The expression "other proteins" relate in particular to other enzymes. The term "purified" as used herein also refers to removal of other components, particularly other proteins and most particularly other enzymes present in the cell of origin of the protease. A protease may be "substantially pure", i.e. substantially free from other components from the organism in which it is produced, e.g., a host organism for recombinantly produced enzyme. Preferably, the protease is at least 75% (w/w) pure, more preferably at least 80%, 85%, 90% or even at least 95% pure. In a still more preferred embodiment the protease is an at least 98% pure enzyme protein preparation.

However, for the uses according to the invention, the protease need not be that pure. It may e.g. include other enzymes, even other proteases, in which case it could be termed a protease preparation.

Use of the protease according to the present invention may be combined with use of other enzymes, e.g. other proteases. In one preferred embodiment, a protease of the endo-type, e.g. the one derived from *Nocardiopsis* sp. NRRL 18262, is combined with an exopeptidase, or a protease preparation having exopeptidase activity, e.g. a protease preparation derived from *Aspergillus oryzae*, as disclosed in WO94/25580, such as FLAVOURZYME® (Novozymes NS, Denmark).

In one particular embodiment, the protease for use according to the invention has a pH-activity optimum close to neutral, when determined by hydrolysis of casein and subsequent reaction of TCA-soluble peptides with o-phtaldialdehyde and 2-mercaptoethanol followed by measurement of the absorbance of the resulting complex at 340 nm.

The term pH-activity optimum close to neutral means one or more of the following: That the pH-optimum is in the interval of pH 5.5-11.0, or pH 7.0-11.0, or pH 6.0-10.0, or pH 7.0-10.0, or pH 8.0-11.0, or pH 8.0-10.0.

In another particular embodiment, the protease for use according to the invention is thermostable.

The term thermostable means one or more of the following: That the temperature optimum is at least 50° C., 52° C., 54° C., 56° C., 58° C., 60° C., 62° C., 64° C., 66° C., 68° C., or at least 70° C., when determined by hydrolysis of casein as described above.

Yeast

Yeast in the context of the present invention may be any kind of yeast. It may belong to the family Saccharomycetaceae. In one particular embodiment, the yeast is a *Saccharomyces*, e.g. *Saccharomyces cerevisiae* or *Saccharomyces uvarum*. In another embodiment, the yeast is a *Kluyveromyces*., e.g. *Kluyveromyces fragilis*. In yet another embodiment, the yeast is *Candida*, e.g. *Candida utilis*, also known as Torula yeast.

The yeast to be applied may be in any form, such as yeast especially grown on e.g. molasses, or spent Brewer's yeast, or yeast collected from alcohol fermentation.

The yeast to be applied may be whole yeast cells or yeast cells which are wholly or partly disrupted or degraded.

Yeast Extract

A yeast extract, which in the context of the present invention is synonymous to yeast hydrolysate or yeast autolysate, is a soluble extract from yeast comprising hydrolysed protein, which is widely used, e.g. as a flavour enhancer.

According to the invention, the yeast extract is produced using exogenous protease for protein hydrolysis. Besides from the added protease, the yeast itself contains a variety of degradative enzymes, including lipases, nucleases, mannanases, glucanases and proteases. The optimum temperatures and pH values for these endogenous enzymes vary, and they may be more or less active under the process conditions according to the present invention.

Before addition of the protease, the yeast may be in the form of an aqueous suspension. The dry matter content of the yeast suspension may be in the range 5-50%, such as 10-30%. The pH and temperature of the yeast suspension may be adjusted paying due regard to the characteristics of the protease in question. In one embodiment, the pH of the yeast suspension is adjusted to be more basic, for example to be in the range of pH 5.5-9, preferably pH 6-8 or more preferably pH 6-7. The adjustment of pH and temperature may take place before, simultaneous with or after the protease is added.

The protease should be applied in an effective amount, i.e. in an amount adequate for sufficient protein hydrolysis. It is at present contemplated that the enzyme is administered in one or more of the following amounts (dosage ranges): 0.001-1; 0.005-1; 0.01-0.5; 0.01-0.2; or 0.01-0.1—all these ranges being in mg enzyme protein per g yeast dry matter.

Before or after addition of the protease, the yeast cells may be disrupted, i.e. by raising the temperature. Optionally, chemicals may be added, such as salt or organic solvents. This process is often referred to as plasmolysis. Plasmolysis and protein hydrolysis caused by the exogenous protease may take place simultaneously.

Self-digestion of the yeast cell contents is often referred to as autolysis. Such self-digestion may take place to varying degrees before or simultaneous with the protein hydrolysis caused by the exogenous protease.

In one preferred embodiment, plasmolysis, protein hydrolysis caused by the exogenous protease and a certain degree of self-digestion takes place simultaneously.

In another embodiment, plasmolysis and self-digestion with the yeast's own enzymes is performed first, and hydrolysis with the added protease is performed in a separate clarification step.

The incubation following addition of protease may take place at any convenient temperature and incubation time necessary for obtaining the desired degree of protein hydrolysis. Protein hydrolysis in the context of this invention may be performed essentially by the added protease or it may be a combination of the action of the added protease and the self-digestive endogenous proteases of the yeast. I.e., the term protein hydrolysis comprises protein hydrolysis performed by the added protease and protein hydrolysis performed by the yeast's own proteases, which is often referred to as autolysis.

In a preferred embodiment, the incubation temperature is in the range of from about 20° C. to about 70° C., preferably from about 40° C. to about 60° C., and the incubation time is in the range of from about 1 hour to 48 hours, preferably 12 to 30 hours.

Both pH and temperature can optionally be adjusted to be either higher or lower at any point in the course of the incubation.

Incubation with protease is continued until the desired result is achieved, following which it may or may not be stopped by inactivating the enzyme, e.g. by a heat-treatment step. Such heat-treatment may also serve to pasteurize the yeast extract.

After the proteolytic treatment, the yeast extract may be separated from the cell debris, e.g. by centrifugation and decantation of the supernatant. The yeast extract thus obtained may be concentrated by any method known in the art.

The quality of the yeast extract can be characterized, e.g. by the following parameters:

The protein yield is the percentage of protein in the yeast dry matter prior to hydrolysis which is recovered in the yeast extract. The following are examples of protein yield obtainable using the proteases of the invention: At least 40%, at least 50%, or at least 60%.

The degree of hydrolysis (DH) expresses the extent of the protein hydrolysis obtained by the method. In the context of this invention, the degree of hydrolysis (DH) is defined by the following formula:

DH=(Number of peptide bonds cleaved/Total number of peptide bonds)×100%

The protein fraction is the fraction of dry solids in the yeast extract which originates from protein. The following are examples of protein fractions obtainable using the proteases of the invention: At least 45%, at least 50%, or at least 55%.

The turbidity of the yeast extract may be determined by any method known in the art. It may be measured as NTU (Nephelometric Turbidity Units). The following are examples of yeast extract turbidity obtainable using the proteases of the invention: Less than 2000 NTU, less than 1500 NTU, less than 1000 NTU, or less than 500 NTU.

One embodiment of the present invention is a yeast extract produced by the method described above.

EXAMPLE 1

Protease from *Nocardiopsis* sp. NRRL 18262 having the sequence shown in SEQ ID NO: 1 was evaluated in comparison with Alcalase and yeast controls without exogenous protease.

*Nocardiopsis* protease and ALCALASE® 2.4 L (Novozymes NS, Denmark) were tested on block yeast from *Saccharomyces cerevisiae*. The yeast was mixed with de-ionized water to reach a dry matter content of 13.7% and was stirred (magnetic) for 60 min. at room temperature. The yeast mixture was heated to 55° C. and a portion was adjusted to pH 6.5. Another portion was not pH adjusted and applied as control (pH in the hydrolysate of the 'Yeast control' was about pH 5). Enzyme was added to samples from the pH adjusted portion. The amount of enzyme was dosed on mg enzyme protein/g yeast dry matter (YDM). 20 ml samples were taken out and the exact amount was weighed. No enzyme was added to the sample termed 'Blank'. Hydrolysis was performed for 22 hours at 55° C. The samples were inactivated for 85° C. for 10 min. After inactivation the samples were centrifuged for 10 min at 3500 rpm using Multifuge 3S-R from Heraeus. The amount of extract was weighed after decantation. Dry solids were measured in the extract by weighing (after drying at 105° C.). The amount of nitrogen in the extract was determined by a combustion method on a Leco FP-528. The amount of protein was calculated as 6.25 times the amount of nitrogen. Free amino nitrogen was determined using an OPA (o-phthaldialdehyde) method. Based on the above measurements the following was calculated:

% Extract Yield=(g extract after centrifugation)/(g yeast mixture before centrifugation)*100%

Protein Yield=(g extract after centrifugation*Protein content in extract)/(g yeast mixture before centrifugation*protein content of yeast mixture) *100%

Protein/DS=(g extract after centrifugation*Protein content in extract)/(g dry solids in extract)*100.

Degree of hydrolysis=(Number of peptide bonds cleaved/total number of peptide bonds)*100=(h/htot)*100

Where h is expressed as a function of meqv serine NH2: h=(serine NH2-0.4)/1; and htot=7.8. Serine NH2 was measured relative to serine standard containing 100 mg/L by measuring absorption at 340 nm.

Turbidity of the extract was measured as NTU (Nephelometric Turbidity Units) by a HACH 2100AN turbidimeter using a USEPA filter. Calibration was performed against a Formazin Turbidity Standard 4000 NTU (available from HACH Company, USA). A higher NTU is a measure of higher turbidity.

| Enzyme | pH in extract | Enzyme dosage mg EP/g YDM | % Protein yield | Degree of hydrolysis | % Prot/% DS | Turbidity (NTU) |
|---|---|---|---|---|---|---|
| Yeast control | 5.12 | 0 | 43.8 | 52.1 | 0.54 | 3789 |
| Blank | 7.08 | 0 | 16.9 | 40.6 | 0.29 | 46.4 |
| Alcalase 2.4 L | 6.91 | 0.022 | 53.7 | 62.5 | 0.51 | 1346 |
| FG | 6.84 | 0.044 | 63.7 | 63.9 | 0.54 | 1937 |
|  | 6.81 | 0.133 | 59.0 | 51.0 | 0.49 | 1821 |
| Protease from | 6.05 | 0.022 | 62.34 | 54.5 | 0.57 | 146 |
| *Nocardiopsis* | 6.40 | 0.044 | 64.68 | 54.9 | 0.57 | 209 |
| sp. NRRL 18262 | 6.91 | 0.133 | 62.74 | 69.0 | 0.54 | 1566 |

The protease from *Nocardiopsis* sp. NRRL 18262 results in a very high protein yield at low dose levels (0.022-0.044 mg EP/g YDM). The turbidity of the *Nocardiopsis* sp. NRRL 18262 protease treated extract is very clear in the same dose range and larger fraction of the dry solids is originating from protein.

The invention claimed is:

1. A method for producing a yeast extract, comprising:
   a) adding to yeast comprising protein a protease having at least 95% identity to SEQ ID NO: 1; and
   b) incubating so as to hydrolyse the protein, and wherein the protease is present at a concentration of between 0.001-1 mg enzyme per g yeast dry matter.

2. The method of claim 1 wherein the yeast is *Saccharomyces*, *Kluveromyces* or *Candida*.

3. The method of claim 1 wherein the yeast is *Saccharomyces cerevisiae* or *Saccharomyces uvarum*.

4. The method of claim 1 wherein the protease is present at a concentration of between 0.005 and 1 mg enzyme per g yeast dry matter.

5. The method of claim 1 wherein the protease is present at a concentration of between 0.01 and 0.5 mg enzyme per g yeast dry matter.

6. The method of claim 1 which further comprises suspending the yeast in an aqueous solution.

7. The method of claim 6 which further comprises adjusting pH of the yeast suspension to be more basic.

8. The method of claim 1 which further comprises performing centrifugation to obtain a precipitate and a supernatant after step b).

9. The method of claim 8 wherein the hydrolysed protein is recovered in the supernatant.

10. The method of claim 1 wherein the protease is present at a concentration of between 0.01-0.2 mg enzyme per g yeast dry matter.

11. The method of claim 1 wherein the protease is present at a concentration of between 0.01-0.1 mg enzyme per g yeast dry matter.

12. The method of claim 1 comprising adding a protease comprising or consisting of the amino acid sequence of SEQ ID NO: 1.

* * * * *